United States Patent [19]

Austel et al.

[11] 4,179,508

[45] Dec. 18, 1979

[54] SULFUR-CONTAINING DERIVATIVES OF 4,4-DIMETHYL-2H,4H-ISOQUINOLINE-1,3-DIONE, AND ANTICONVULSANT AND ANTIHYPERLIPIDEMIC COMPOSITIONS THEREOF

[75] Inventors: Volkhard Austel; Eberhard Kutter; Wolfgang Eberlein, all of Biberach; Joachim Heider, Warthausen; Joachim Kähling, Biberach, all of Fed. Rep. of Germany

[73] Assignee: Boehringer Ingelheim GmbH, Ingelheim am Rhein, Fed. Rep. of Germany

[21] Appl. No.: 925,877

[22] Filed: Jul. 18, 1978

[30] Foreign Application Priority Data

Jul. 29, 1977 [DE] Fed. Rep. of Germany ....... 2734222

[51] Int. Cl.$^2$ .................... C07D 217/24; A61K 31/47
[52] U.S. Cl. ...................... 424/258; 546/142
[58] Field of Search .................... 260/281 R; 424/258; 546/142

[56] References Cited

U.S. PATENT DOCUMENTS

| 3,708,486 | 1/1973 | Kulter et al. ............... 260/281 R |
| 3,946,017 | 3/1976 | Schefczik et al. ............ 260/281 R |

*Primary Examiner*—Mark L. Berch
*Attorney, Agent, or Firm*—Hammond & Littell

[57] ABSTRACT

Compounds of the formula

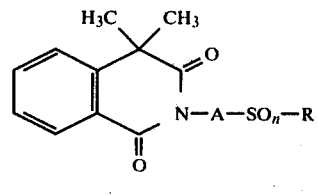

wherein
A is lower alkylene,
R is lower alkyl, and
n is 0, 1 or 2;

the compounds are useful as anti-hyperlipidemics and anti-convulsants.

9 Claims, No Drawings

SULFUR-CONTAINING DERIVATIVES OF 4,4-DIMETHYL-2H,4H-ISOQUINOLINE-1,3-DIONE, AND ANTICONVULSANT AND ANTIHYPERLIPIDEMIC COMPOSITIONS THEREOF

This invention relates to novel sulfur-containing derivatives of 4,4-dimethyl-2H,4H-isoquinoline-1,3-dione, as well as to methods of preparing these compounds, pharmaceutical compositions containing them, and methods of using them for the treatment of hyperlipidemia and as anticonvulsants.

More particularly, the present invention relates to a novel class of compounds represented by the formula

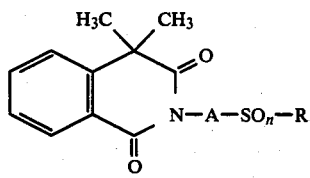

wherein
A is lower alkylene,
R is lower alkyl, and
n is 0, 1 or 2.

The term "lower alkylene" as used herein is intended to mean alkylene of 1 to 6 carbon atoms, and preferably straight or branched alkylene of 1 to 4 carbon atoms. Similarly, the term "lower alkyl" is intended to mean alkyl of 1 to 6 carbon atoms, and preferably straight or branched alkyl of 1 to 4 carbon atoms.

Thus, a sub-genus under the genus defined by formula I is constituted by those compounds where A is straight or branched alkylene of 1 to 4 carbon atoms, R is straight or branched alkyl of 1 to 4 carbon atoms, and n is 0, 1 or 2.

Examples of specific embodiments of variables A and R in formula I are the following:
A—methylene, ethylidene, propylidene, dimethylmethylene, ethylene, methyl-ethylene, propylene, dimethyl-ethylene, methyl-propylene and butylene.
R—methyl, ethyl, n-propyl, isopropyl, n-butyl, isobutyl, sec. butyl and tert. butyl.

A still further sub-genus under the genus defined by formula I is constituted by those compounds where A is methylene, ethylene, or propylene, R is methyl, isopropyl or butyl, and n is 0, 1 or 2.

The compounds embraced by formula I may be prepared by the following methods:

Method A

For the preparation of a compound of the forumla I wherein n is 0, by reacting the homophthalimide of the formula

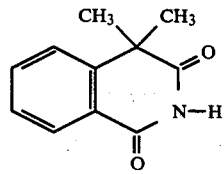

or an alkali metal salt thereof with a thioether of the formula

Z—A—S—R  (III)

wherein
A and R have the same meanings as in formula I, and
Z is an exchangeable substituent, such as chlorine, bromine, iodine, alkylsulfonyloxy or arylsulfonyloxy.

The reaction is optionally carried out in a solvent, such as acetone, isopropanol, dimethylformamide, dimethylsulfoxide or toluene, and, depending on the reactivity of the substituent Z, at temperatures between 0° and 150° C., but preferably at the boiling point of the particular solvent which is used. The presence of an acid-binding agent, for instance an alcoholate, such as sodium isopropylate or potassium tert. butylate, an alkali metal hydroxide, an alkali metal carbonate, an alkali metal amide or a tertiary organic base, such as triethylamine or pyridine, or of a reaction accelerator, such as potassium iodide, is of advantage.

Method B

For the preparation of a compound of the formula I wherein n is 0, by reacting a 2-alkyl-4,4-dimethyl-isoquinoline-1,3-dione of the formula

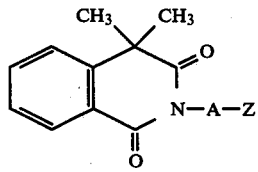

wherein
A has the same meanings as in formula I, and
Z has the same meanings as in formula III, with a mercaptan of the formula

H—S—R  (V)

wherein R has the same meanings as in formula I, or an alkali metal salt thereof.

The reaction is optionally carried out in a solvent, such as tetrahydrofuran, ethanol, isopropanol, dimethylformamide, dimethylsulfoxide or toluene, and, depending on the reactivity of the substitute Z, at temperatures between 0° and 150° C., but preferably at the boiling point of the particular solvent which is used. The presence of an acid-binding agent, for instance an alcoholate, such as sodium ethylate, or an alkali metal hydroxide, an alkali metal carbonate, an alkali metal amide or a tertiary organic base, such as triethylamine or pyridine, or of a reaction accelerator, such as potassium iodide, is of advantage.

Method C

For the preparation of a compound of the formula I wherein n is 1 or 2, by oxidizing an N-substituted 4,4-dimethyl-isoquinoline-1,3-dione of the formula

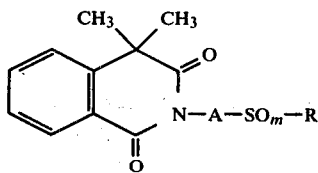

wherein

A and R have the same meanings as in formula I, and m is 0 or 1.

The oxidation is preferably carried out in a solvent, for example in water, water/pyridine, glacial acetic acid, dilute sulfuric acid or trifluoro-acetic acid, and depending on the particular oxidizing agent which is used, at temperatures between $-80°$ and $100°$ C.

For the preparation of a compound of the formula I wherein n is 1, the oxidation is carried out with one equivalent of the oxidizing agent; for example, with hydrogen peroxide in glacial acetic acid at $0°$ to $20°$ C.; with a peracid such as peracetic acid, chloro-perbenzoic acid or peroxytrifluoro acetic acid at $0°$ to $50°$ C.; with sodium metaperiodate in aqueous methanol or ethanol at $15°$ to $25°$ C.; with tert. butyl hypochlorite in methanol at $-80°$ to $-30°$ C.; with iodobenzene dichloride in aqueous pyridine at $0°$ to $50°$ C.; with nitric acid in glacial acetic acid at $0°$–$20°$ C.; with chromic acid in glacial acetic acid or in acetone at $0°$ to $20°$ C.; or with sulfurylchloride in methylene chloride at $-70°$ C., where the thus obtained thioether-chloro-complex is hydrolized with aqueous ethanol.

For the preparation of a compound of the formula I wherein n is 2, the oxidation is carried out with one or two equivalents of the oxidizing agent; for example with hydrogen peroxide in glacial acetic acid at $20°$ to $100°$ C.; with a peracid, such as peracetic acid, m-chloroperbenzoic acid or peroxytrifluoro-acetic acid, at temperatures between $0°$ and $20°$ C.; or with chromic acid or potassium permanganate in glacial acetic acid, water/sulfuric acid or in acetone at $0°$ to $20°$ C. If m in a compound of the formula VI is 0, the reaction is preferably carried out with two equivalents of the corresponding oxidizing agent, and if m is 1 quite correspondingly with one equivalent.

The starting compounds of the formulas II–V can be obtained by known methods, or they are described in the literature. The starting compounds of the general formula VI can be obtained by methods A to C above.

The above-described methods may be used to prepare the following compounds, for example:

4,4-Dimethyl-2-(methylmercapto-methyl)-2H,4H-isoquinoline-1,3-dione,
4,4-Dimethyl-2-(methylsulfinyl-methyl)-2H,4H-isoquinoline-1,3-dione,
4-Dimethyl-2(2-methylmercapto-ethyl)-2H,4H-isoquinoline-1,3-dione,
4,4-Dimethyl-2-(2-methylsulfinyl-ethyl)-2H,4H-isoquinoline-1,3-dione,
4,4-Dimethyl-2-(2-methylsulfonyl-ethyl)-2H,4H-isoquinoline-1,3-dione,
4,4-Dimethyl-2-(4-butylmercapto-butyl)-2H,4H-isoquinoline-1,3-dione,
4,4-Dimethyl-2-(4-butylsulfinyl-butyl)-2H,4H-isoquinoline-1,3-dione,
4,4-Dimethyl-2-(4-butylsulfonyl-butyl)-2H,4H-isoquinoline-1,3-dione,
4,4-Dimethyl-2-(ethylmercapto-methyl)-2H,4H-isoquinoline-1,3-dione,
4,4-Dimethyl-2-(isopropylsulfonyl-methyl)-2H,4H-isoquinoline-1,3-dione,
4,4-Dimethyl-2-(ethylsulfinyl-methyl)-2H,4H-isoquinoline-1,3-dione,
4,4-Dimethyl-2-(2-ethylmercapto-ethyl)-2H,4H-isoquinoline-1,3-dione,
4,4-Dimethyl-2-(2-propylmercapto-ethyl)-2H,4H-isoquinoline-1,3-dione,
4,4-Dimethyl-2-(isopropylmercapto-methyl)-2H,4H-isoquinoline-1,3-dione,
4,4-Dimethyl-2-(3-isopropylmercapto-propyl)-2H,4H-isoquinoline-1,3-dione.
4,4-Dimethyl-2-(3-tert.butylmercapto-propyl)-2H,4H-isoquinoline-1,3-dione,
4,4-Dimethyl-2-(2-ethylsulfinyl-ethyl)-2H,4H-isoquinoline-1,3-dione,
4,4-Dimethyl-2-(2-propylsulfinyl-ethyl)-2H,4H-isoquinoline-1,3-dione,
4,4-Dimethyl-2-(isopropylsulfinyl-methyl)-2H,4H-isoquinoline-1,3-dione,
4,4-Dimethyl-2-(3-isopropylsulfinyl-propyl)-2H,4H-isoquinoline-1,3-dione,
4,4-Dimethyl-2-(3-tert.butylsulfinyl-propyl)-2H,4H-isoquinoline-1,3-dione,
4,4-Dimethyl-2-(2-ethylsulfonyl-ethyl)-2H,4H-isoquinoline-1,3-dione,
4,4-Dimethyl-2-(2-propylsulfonyl-ethyl)-2H,4H-isoquinoline-1,3-dione,
4,4-Dimethyl-2-(3-isopropylsulfonyl-propyl)-2H,4H-isoquinoline-1,3-dione, and
4,4-Dimethyl-2-(3-tert.butylsulfonyl-propyl)-2H,4H-isoquinoline-1,3-dione.

The following examples illustrate the present invention and will enable others skilled in the art to understand it more completely. It should be understood, however, that the invention is not limited solely to the particular examples given below.

EXAMPLE 1

4,4-Dimethyl-2-(2-methylmercapto-ethyl)-2H,4H-isoquinoline-1,3-dione by method A 11.4 gm of potassium tert.butylate were added to a solution of 18 gm of 4,4-dimethyl-2H,4H-isoquinoline-1,3-dione in 70 ml of dimethylformamide, and the mixture was stirred for 5 minutes at room temperature. 11.1 gm of 1-chloro-2-methylmercapto-ethane were then added, and the mixture was heated at $80°$ C. for 2 hours. After distilling off the dimethylformamide in vacuo, the residue was taken up in chloroform and water. The organic phase was separated and evaporated, and the residue was purified on a silicagel column (eluant: chloroform), yielding 23.1 gm (87.7% of theory) of an oily product which was identified to be the compound of the formula

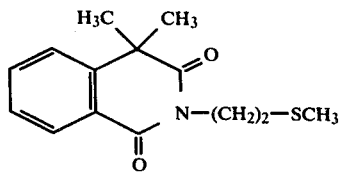

Elemental Analysis: Calc.: C-63.85%; H-6.51%; N-5.32%; S-12.17%: Found: C-64.10%; H-6.53%; N-5.68%; S-12.37%.

EXAMPLE 2

4,4-Dimethyl-2-(2-methylmercapto-ethyl)-2H,4H-isoquinoline-1,3-dione by method A 5.7 gm of 4,4-dimethyl-2H,4H-isoquinoline-1,3-dione and 3.3 gm of 1-chloro-2-methylmercapto-ethane were added to a solution of 0.7 gm of sodium in 200 ml of isopropanol. After refluxing the mixture for 3 hours the solvent was removed in vacuo, and the residue was taken up in water and chloroform. The separated organic phase was worked up as described in Example 1. Yield: 7 gm (88.6% of theory).

EXAMPLE 3

4,4-Dimethyl-2-(2-methylsulfinyl-ethyl)-2H,4H-isoquinoline-1,3-dione by method C 6.9 ml of 30% hydrogen peroxide were added to a solution of 16 gm of 4,4-dimethyl-2-(2-methylmercapto-ethyl)-2H,4H-isoquinoline-1,3-dione in 30 ml of glacial acetic acid, while maintaining the temperature between 20° and 40° C. After 15 minutes the reaction mixture was poured into water, and the resulting mixture was neutralized with ptoassium carbonate and extracted with chloroform. The chloroform phase was evaporated, the residue was purified on a silicagel column (eluant: chloroform/acetone 19:1), and after evaporation of the eluate the residue was recrystallized from cyclohexane by addition of seed crystals.
Yield: 15.6 gm (92% of theory); M.p.: 84°–85° C.

EXAMPLE 4

4,4-Dimethyl-2-(2-methylsulfonyl-ethyl)-2H,4H-isoquinoline-1,3-dione by method C 5.7 ml of 30% hydrogen peroxide were added to a solution of 3.95 gm of 4,4-dimethyl-2-(2-methylmercapto-ethyl)-2H,4H-isoquinoline-1,3-dione in 20 ml of glacial acetic acid. After heating the mixture at 55°–60° C. for 3 hours it was admixed with water, neutralized with potassium carbonate and extracted with chloroform. The chloroform extracts were evaporated, and the residue was recrystallized from toluene.
Yield 4.1 gm (92.6% of theory); M.p. 145°–146° C.

EXAMPLE 5

4,4-Dimethyl-2-(4-butylmercapto-butyl)-2H,4H-isoquinoline-1,3-dione by method B 1 gm of sodium was dissolved in 100 ml of ethanol, 3.7 gm of n-butylmercaptan were added dropwise to the solution, and a solution of 12 gm of 4,4-dimethyl-2-(4-chloro butyl)-2H,4H-isoquinoline-1,3-dione was slowly added. After refluxing the mixture for 3 hours, the precipitate was filtered off, the filtrate was evaporated, the residue was poured into ice water, and the aqueous mixture was acidified and extracted with chloroform. The chloroform phases were evaporated, whereby an oily crude product was obtained (13.0 gm, 98% of theory), which was purified by chromatography on silicagel (eluant: chloroform).
Yield: 3.8 gm (34% of theory). Calc.: C-68.40%; H-8.12%; N-4.20%; S-9.62%: Found: C-68.00%; H-8.08%; N-4.47%; S-9.41%.

EXAMPLE 6

4,4-Dimethyl-2-(4-butylsulfinyl-butyl)-2H,4H-isoquinoline-1,3-dione

Prepared analogous to Example 3 from 3.3 gm of 4,4-dimethyl-2-(4-butylmercapto-butyl)-2H,4H-isoquinoline-1,3-dione. (reaction temperature: 20°–25° C.; reaction time: 1.5 hours). The obtained product was a colorless oil.
Yield: 2 gm (57.3% of theory).
Calc.: C-65.30%; H-7.79%; N-4.00%; S-9.15%: Found: C-64.40%; H-7.78%; N-3.94%; S-9.19%.

EXAMPLE 7

4,4-Dimethyl-2-(4-butylsulfonyl-butyl)-2H,4H-isoquinoline-1,3-dione

Prepared analogous to Example 4 from 6.7 gm of 4,4-dimethyl-2-(4-butylmercapto-butyl)-2H,4H-isoquinoline-1,3-dione.
Yield: 5.0 gm (68.5% of theory); M.p.: 84°–87° C.

EXAMPLE 8

4,4-Dimethyl-2-(methylmercapto-methyl)-2H,4H-isoquinoline-1,3-dione by method B 1.92 gm of methylmercaptan were added to an ice-cooled solution of 0.92 gm of sodium in 50 ml of ethanol. A suspension of 8.6 gm of 4,4-dimethyl-2-chloromethyl-2H,4H-isoquinoline-1,3-dione in 100 ml of ethanol was added, and the mixture was refluxed for 45 minutes. Thereafter, the reaction mixture was evaporated, the residue was triturated with water, filtered, the filter cake was recrystallized from isopropanol.
Yield: 3.5 gm (39.1% of theory). M.p.: 90° C.

EXAMPLE 9

4.4-Dimethyl-2-(methylsulfinyl-methyl)-2,4H-isoquinoline-1,3-dione by method C

A solution of 0.5 gm of 30% hydrogen peroxide in 20 ml of glacial acetic acid was added to a solution of 1.25 gm of 4,4-dimethyl-2-(methylmercapto-methyl)-2H,4H-isoquinoline-1,3-dione in 30 ml of glacial acetic acid, and the mixture was stirred for 6 hours at room temperature. Thereafter, the reaction mixture was poured over ice, and the resulting aqueous mixture was made alkaline with ammonia while cooling, whereby part of the product precipitated in crystalline form and was suction-filtered off. The filtrate was extracted with chloroform, and the extract solution was evaporated, whereby a further fraction of the product was obtained.
Yield: 1 gm (75.8% of theory); M.p.: 82° C. (from water).

EXAMPLE 10

4,4-Dimethyl-2(methylsulfonyl-methyl)-2H,4H-isoquinoline-1,3-dione by method C

A solution of 0.46 gm of 30% hydrogen peroxide in 5 ml of glacial acetic acid was added to a solution of 1 gm of 4,4-dimethyl-2-(methylmercapto-methyl)-2H,4H-isoquinoline-1,3-dione in 15 ml of glacial acetic acid, and the mixture was heated at 40° C. for 16 hours. 0.5 ml of 30% hydrogen peroxide was now added, and heating was continued for 7 hours more. The reaction mixture was then poured over ice, and the pH of the aqueous mixture was adjusted to 5 by addition of concentrated ammonia. After standing for several hours at 3° C., the product separated out in crystalline form.

Yield: 0.6 gm (53.5% of theory); M.P.: 150° C. (from ethanol).

EXAMPLE 11

4,4 Dimethyl-2-(isopropylmercapto-methyl)-2H,4H-isoquinoline-1,3 dione by method B 1.17 gm of isopropylmercaptan were added to a solution of 0.83 gm of sodium methylate in 50 ml of methanol. After shaking the resulting mixture, 3.3 gm of 4,4-dimethyl-2-chloromethyl-2H,4H-isoquinoline-1,3-dione were added, and the mixture was refluxed for 15 minutes. The precipitated sodium chloride was suction-filtered off, the filtrate was evaporated, and the residue was purified on a silicagel column (eluant: chloroform-/cyclohexane=1:1). After evaporation of the eluate a colorless oil was obtained.

Yield: 3.85 gm (100% of theory). Calc.: C-64.97%; H-6.91%; N-5.05%; S-11.50%: Found: C-65.20%; H-6.90%, N-5.18%; S-11.34%.

EXAMPLE 12

4,4-Dimethyl-2-(isopropylsulfinyl-methyl)-2H,4H-isoquinoline-1,3-dione

Prepared analogous to Example 9 from 1.8 gm of 4,4-dimethyl-2-(isopropylmercapto-methyl)-2H,4H-isoquinoline-1,3-dione.

Yield: 1.4 gm (74% of theory); M.p.: 86°–89° C.

EXAMPLE 13

4,4-Dimethyl-2-(isopropylsulfonyl-methyl)-2H,4H-isoquinoline-1,3-dione

Prepared analogous to Example 10 from 1.4 gm of 4,4-dimethyl-2-(isopropylmercapto-methyl)-2H,4H-isoquinoline-1,3-dione.

Yield: 1.3 gm (82% of theory); M.P.: 89°–93° C.

The compounds of the present invention, that is, those embraced by formula I above, have useful pharmacodynamic properties. More particularly, they exhibit anticonvulsive and anti-hyperlipidexmic activities in warm-blooded animals, such as mice.

The anticonvulsive activity and toxicity of the compounds of this invention were ascertained by the methods described below, and tables I and II show the results of these tests for a few representative species of the genus, where A=4,4-Dimethyl-2-(2-methylmercapto-ethyl)-2H,4H-isoquinoline-1,3-dione, B=4,4-Dimethyl-2-(2-methylsulfinyl-ethyl)-2H,4H-isoqionoline-1,3-dione, C=4,4-Dimethyl-2-(2-methylsulfonyl-ethyl)-2H,4H-isoquinoline-1,3-dione, D=4,4-Dimethyl-2-(methylmercapto-methyl)-2H,4H-isoquinoline-1,3-dione and E=4,4-Dimethyl-2-(methylsulfinyl-methyl)-2H,4H-isoquinoline-1,3-dione.

1. Anticonvulsive activity in mice

Male mice with body weights of between 20 and 26 gm were used as the test animals. They were allowed free access to food and water up to one hour before administration of the test compound. The tests were carried out by using the maximal electroshock seizure pattern method [SWINYARD et, J. Pharmacol. exp. Ther. 106, 319 (1952)].

The electroshock apparatus was constructed according to WOODBURY and DAVENPORT [Arch. int. Pharmacodyn. 99, 97 (1952)]. The electric impulses (50 Hz A.C., 50 mA, 0.2 sec.) were delivered via steel ball electrodes covered with buckskin and moistened with an aqueous 0.9% sodium chloride solution to the heads by way of the eyes of the mice. The test is a measure of the ability of an anticonvulsant drug to abolish the hind limb tonic extensor component of the maximal seizure pattern induced by electric stimulation. The test compound was suspended in 1% of tylose and administered orally in a volume of 0.1 ml per 10 gm of mouse, and each dosage was administered to a group of 10 animals. Control groups received the suspension agent orally. 30, 150 and 300 minutes after administration all animals were shocked. $ED_{50}$ values were determined by the graphic statistical method of LITCHFIELD and WILCOXON [J. Pharmacol. exp. Therap. 96, 99 (1949)] as a measure of the ability of the test compounds to abolish the hindlimb tonic extensor compound of the maximal seizure pattern in 50 percent of the animals.

Table I

| Compound | $ED_{50}$ mg/kg p.o. | | |
|---|---|---|---|
| | 30 | 150 | 300 minutes |
| A | 17.3 | 22.8 | 27.8 |
| B | 14.5 | 16.8 | 25.0 |
| C | 26.3 | 35.2 | 32.5 |
| D | 28 | 16.2 | 19.8 |
| E | 8.3 | 10.5 | 11.5 |

2. Acute toxicity

The acute toxicity of the compounds was determined after administration of various dosages to groups of 10 mice with body weights of between 20 and 26 gm (observation time: 4 days).

Table II

| Compound | Acute toxicity |
|---|---|
| A | > 500 mgm/kg p.o. (0 of 10 animals died) |
| B | ~ 500 mgm/kg p.o. (4 of 10 animals died) |
| C | > 500 mgm/kg p.o. (1 of 10 animals died) |

The test data tabulated above indicate that the compounds of the formula I prepared according to the invention are suitable particularly for the treatment of spastic conditions and epilepsy.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 5.0 mgm/kg body weight, preferably 0.83 to 3.3 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 14

Tablets

The tablet composition is compounded from the following ingredients:

| | |
|---|---|
| 4,4-Dimethyl-2-(2-methylsulfinyl-ethyl)-2H,4H-isoquinoline-1,3-dione | 100.0 parts |
| Lactose | 50.0 parts |
| Polyvinylpyrrolidone | 5.0 parts |
| Carboxymethyl cellulose | 19.0 parts |
| Magnesium stearate | 1.0 parts |
| Total | 175.0 parts |

Preparation

The active ingredient is intimately admixed with the lactose and the polyvinylpyrrolidone, the mixture is granulated by moist screening through a 1.5 mm-mesh screen, the granulate is dried at 50° C. in a circulating air dryer, and the dry granulate is again passed through a 1.0 mm-mesh screen. The magnesium stearate and the carboxymethyl cellulose are then blended into the granulate, and the resulting composition is compressed into 175 mgm-tablets. Each tablet is an oral dosage unit composition containing 100 mgm of the active ingredient.

EXAMPLE 15

Coated Pills

The pill core composition is compounded from the following ingredients:

| | |
|---|---|
| 4,4-Dimethyl-2-(2-methylsulfinyl-ethyl-2H,4H-isoquinoline-1,3-dione | 50.0 parts |
| Corn starch, dried | 20.0 parts |
| Soluble starch | 2.0 parts |
| Carboxymethyl cellulose | 7.0 parts |
| Magnesium stearate | 1.0 parts |
| Total | 80.0 parts |

Preparation

The active ingredient and the corn starch are intimately admixed with each other, the mixture is moistened with an aqueous solution of the soluble starch and granulated through a 1.0 mm-mesh screen, the granulate is dried at 50° C. in a circulating air dryer, and the dry granulate is again passed through the above screen. The carboxymethyl cellulose and the magnesium stearate are then blended into the granulate, and the resulting composition is compressed into 80 mgm-pill cores which are subsequently coated with a thin shell consisting essentially of sugar and talcum. Each coated pill is an oral dosage unit composition containing 50 mgm of the active ingredient.

EXAMPLE 16

Suppositories

The suppository composition is compounded from the following ingredients:

| | |
|---|---|
| 4,4-Dimethyl-2-(2-methylsulfinyl-ethyl)-2H,4H-isoquinoline-1,3-dione | 200.0 parts |
| Suppository base (e.g. coca butter) | 1500.0 parts |
| Total | 1700.0 parts |

PREPARATION

The suppository base is melted, cooled to 38° C., and the pulverized active ingredient is homogeneously dispersed therein. The composition is then cooled to 35° C., and 1700 mgm-portions thereof are poured into cooled suppository molds and allowed to harden therein. Each suppository is a rectal dosage unit composition containing 200 mgm of the active ingredient.

EXAMPLE 17

Suspension

The suspensions is compounded from the following ingredients:

| | |
|---|---|
| 4,4-Dimethyl-2-(2-methylsulfinyl-ethyl)-2H,4H-isoquinoline-1,3-dione | 5.0 parts |
| carboxymethyl cellulose | 0.1 parts |
| p-Hydroxy-benzoic acid methyl ester | 0.05 parts |
| p-Hydroxy-benzoic acid propyl ester | 0.01 parts |
| cane sugar | 10.0 parts |
| Glycerin | 5.0 parts |
| Sorbitol solution 70% | 20.0 parts |
| Flavoring | 0.3 parts |
| Distilled water q.s.ad | 100.0 parts by vol. |

Preparation

The distilled water is heated to 70° C., and the p-hydroxy-benzoates, the glycerin and the carboxymethyl cellulose are dissolved therein while stirring. The solution is cooled to room temperature, and the active ingredient is added and homogeneously dispersed therein by stirring. After adding the sugar, the sorbitol solution and the flavoring, the suspension is de-aerated by stirring in vacuo. 5 ml of the suspension are an oral dosage unit composition containing 250 mgm of the active ingredient.

Any one of the other compounds embraced by formula I may be substituted for the particular active ingredient in Examples 14 through 17. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

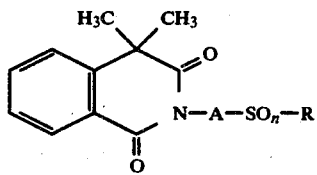

where
A is lower alkylene,
R is a lower alkyl, and
n is 0, 1 or 2.

2. A compound of claim 1,
where
A is alkylene of 1 to 4 carbon atoms,
R is alkyl of 1 to 4 carbon atoms, and
n is 0, 1 or 2.

3. A compound of claim 1,
wherein
A is methylene, ethylene, or propylene,
R is methyl, isopropyl or butyl, and
n is 0, 1 or 2.

4. The compound of claim 3, which is 4,4-dimethyl-2-(2-methylmercapto-ethyl)-2H,4H-isoquinoline-1,3-dione.

5. The compound of claim 3, which is 4,4-dimethyl-2-(2-methylmercapto-methyl)-2H,4H-isoquinoline-1,3-dione.

6. The compound of claim 3, which is 4,4-dimethyl-2-(2-methylsulfinyl-ethyl)-2H,4H-isoquinoline-1,3-dione.

7. The compound of claim 3, which is 4,4-dimethyl-2-(2-methylsulfonyl-methyl)-2H,4H-isoquinoline-1,3-dione.

8. An anticonvulsant or antihyperlipidemic pharmaceutical dosage unit composition consisting essentially of an inert pharmaceutical carrier and an effective anticonvulsant or antihyperlipidemic amount of a compound of claim 1.

9. The method of suppressing convulsions or lowering the level of lipids in the blood in a warm-blooded animal in need thereof, which comprises perorally, parenterally or rectally administering to said animals an effective anticonvulsant or antihyperlipidemic amount of a composition of claim 8.

* * * * *